(12) United States Patent
Arnholt et al.

(10) Patent No.: US 8,577,463 B2
(45) Date of Patent: *Nov. 5, 2013

(54) INTERCONNECTED ELECTRODE ASSEMBLY FOR A LEAD CONNECTOR AND METHOD THEREFOR

(75) Inventors: Devon N. Arnholt, Minneapolis, MN (US); Michelle Fangmeier, Blaine, MN (US); Samir Rajnibhai Gami, Savage, MN (US); Aaron Gebauer, St. Paul, MN (US); Kyle Hoecke, Lino Lakes, MN (US); Weston Pernsteiner, Marquette, MI (US); Gregory L. Sundberg, Stillwater, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 171 days.

This patent is subject to a terminal disclaimer.

(21) Appl. No.: 13/100,558

(22) Filed: May 4, 2011

(65) Prior Publication Data
US 2011/0208282 A1  Aug. 25, 2011

Related U.S. Application Data

(63) Continuation of application No. 11/128,123, filed on May 12, 2005, now Pat. No. 7,962,213.

(51) Int. Cl.
*A61N 1/375* (2006.01)
(52) U.S. Cl.
USPC .......................................................... 607/37
(58) Field of Classification Search
USPC ....................................................... 607/116
See application file for complete search history.

(56) References Cited

U.S. PATENT DOCUMENTS

| | | | |
|---|---|---|---|
| 3,657,744 A | 4/1972 | Ersek | |
| 5,056,517 A | 10/1991 | Fenici | |
| 5,304,219 A | 4/1994 | Chernoff et al. | |
| 5,385,409 A | 1/1995 | Ide | |
| 5,487,757 A | 1/1996 | Truckai et al. | |
| 5,669,790 A | 9/1997 | Carson et al. | |
| 6,026,567 A | 2/2000 | Swoyer et al. | |
| 6,434,430 B2 | 8/2002 | Borgersen et al. | |
| 6,623,480 B1 | 9/2003 | Kuo et al. | |
| 6,650,921 B2 | 11/2003 | Spehr et al. | |
| 6,725,096 B2 | 4/2004 | Chinn et al. | |
| 6,785,576 B2 | 8/2004 | Verness | |
| 6,792,317 B1 | 9/2004 | Doan et al. | |
| 6,912,423 B2 | 6/2005 | Ley et al. | |
| 7,160,311 B2 | 1/2007 | Blatter et al. | |
| 7,175,478 B2 | 2/2007 | Ollivier | |
| 7,234,977 B2 | 6/2007 | Westlund et al. | |
| 7,648,401 B2 | 1/2010 | Guenther et al. | |
| 7,962,213 B2* | 6/2011 | Arnholt et al. | ................... 607/37 |
| 8,126,557 B2 | 2/2012 | Jang et al. | |

(Continued)

OTHER PUBLICATIONS

International Search Report and Written Opinion issued in PCT/US2010/057025 dated Mar. 2, 2011.

*Primary Examiner* — Christopher D Koharski
*Assistant Examiner* — Jeremiah Kimball
(74) *Attorney, Agent, or Firm* — Faegre Baker Daniels LLP (57) ABSTRACT

An electrode assembly includes an interconnect for at least a first connector electrode and a second connector electrode, where the interconnect provides the mechanical and/or electrical connection between the electrodes. In one example, the assembly is an elongate member having material removed therefrom along an intermediate portion.

20 Claims, 7 Drawing Sheets

(56) References Cited

U.S. PATENT DOCUMENTS

| | | |
|---|---|---|
| 2001/0037135 A1 | 11/2001 | Pianca et al. |
| 2002/0029074 A1 | 3/2002 | Treaba et al. |
| 2002/0077685 A1 | 6/2002 | Sundquist et al. |
| 2003/0023294 A1 | 1/2003 | Krall et al. |
| 2003/0036779 A1 | 2/2003 | Westlund et al. |
| 2003/0074031 A1 | 4/2003 | Ley et al. |
| 2004/0054390 A1 | 3/2004 | Zarembo et al. |
| 2004/0064174 A1 | 4/2004 | Belden |
| 2004/0068313 A1 | 4/2004 | Jenney et al. |
| 2004/0215282 A1 | 10/2004 | Weijden et al. |
| 2004/0215303 A1 | 10/2004 | Sage |
| 2004/0230268 A1 | 11/2004 | Huff et al. |
| 2005/0027325 A1 | 2/2005 | Lahti et al. |
| 2006/0041299 A1 | 2/2006 | Bauer et al. |
| 2006/0259105 A1 | 11/2006 | Gebauer et al. |
| 2007/0027517 A1 | 2/2007 | Bischoff et al. |
| 2008/0027504 A1 | 1/2008 | Bedenbaugh |
| 2008/0046059 A1 | 2/2008 | Zarembo et al. |
| 2008/0114230 A1 | 5/2008 | Addis |
| 2008/0154328 A1 | 6/2008 | Thompson et al. |
| 2011/0159748 A1 | 6/2011 | Lim et al. |

\* cited by examiner

INTERCONNECTED ELECTRODE ASSEMBLY FOR A LEAD CONNECTOR AND METHOD THEREFOR

CROSS-REFERENCE TO RELATED APPLICATION

"This application is a continuation of U.S. application Ser. No. 11/128,123, filed May 12, 2005 (now U.S. Pat. No. 7,962, 213), which is incorporated herein by reference in its entirety for all purposes."

TECHNICAL FIELD

Electrode assemblies for leads which conduct electrical signals to and from the heart, and more particularly, an interconnected electrode assembly for an in-line multipolar lead connector.

BACKGROUND

Pacemaker leads represent the electrical link between the pulse generator and the heart tissue, which is to be excited and/or sensed. These pacemaker leads include single or multiconductors that are connected to an electrode in an electrode assembly at an intermediate portion or distal end of a pacing lead. A connector is included at the proximal end to form the electrical connection with the pacemaker.

When leads with multiple conductors are involved, the conductors are individually, mechanically and electrically coupled with the pulse generator at a proximal end of the multiple conductors. The multiple conductors at the proximal end are electrically insulated from each other to prevent shorts and limit electrical leakage between conductors. Some therapies require electrical connection between two or more conductors somewhere along the lead. In creating these connections, some conventional assemblies can have manufacturing drawbacks, for example, the assembly process is complex and time consuming, for example in the joining processes.

Accordingly, what is needed is an improved electrode assembly that overcomes these drawbacks.

SUMMARY

A connector apparatus includes a lead connector having a electrode assembly with at least a first electrode and a second electrode, and at least one electrode interconnect mechanically and electrically interconnected between the first electrode and the second electrode. The one, two, three or more electrode interconnects substantially fixate the first electrode and the second electrode longitudinally to one another, or prevent longitudinal and/or rotational movement of the first electrode relative to the second electrode. In an example, the electrode assembly is a unitary piece of material.

A method for forming the electrode assembly is further provided herein. The method includes providing an elongate structure of electrically conductive material, where the elongate structure extends from a first end to a second end and defined in part by an outer perimeter. The method further includes removing a first portion of the outer perimeter of the elongate structure and forming an interconnect between the first end and the second end.

These and other embodiments, aspects, advantages, and features will be set forth in part in the description which follows, and in part will become apparent to those skilled in the art by reference to the following description and referenced drawings or by practice thereof. The aspects, advantages, and features are realized and attained by means of the instrumentalities, procedures, and combinations particularly pointed out in the appended claims and their equivalents.

DETAILED DESCRIPTION

In the following detailed description, reference is made to the accompanying drawings, which form a part hereof, and in which is shown by way of illustration specific embodiments in which the invention may be practiced. These embodiments are described in sufficient detail to enable those skilled in the art to practice the invention, and it is to be understood that other embodiments may be utilized and that structural changes may be made without departing from the spirit and scope of the present invention. Therefore, the following detailed description is not to be taken in a limiting sense, and the scope is defined by the appended claims.

Figure 1:
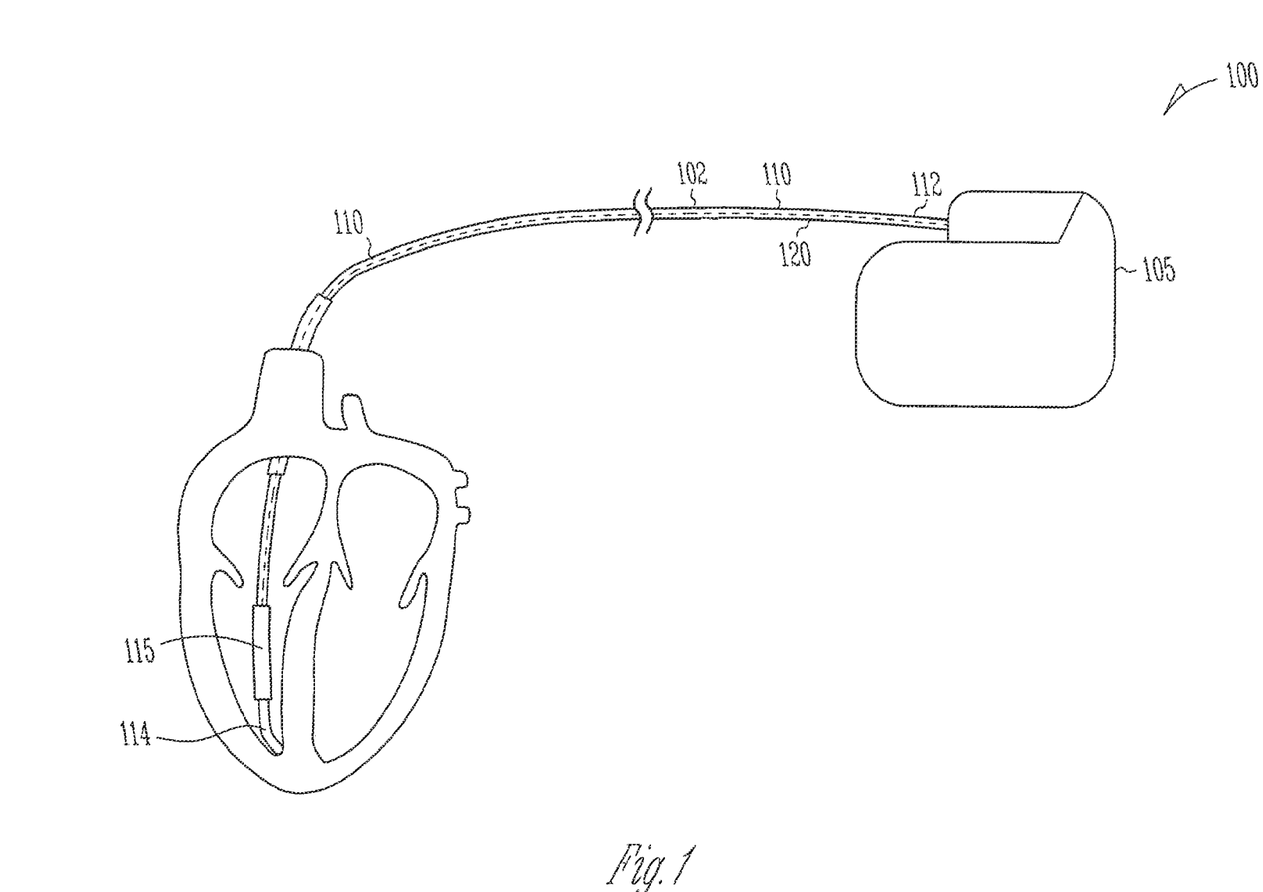
FIG. 1 is a diagram illustrating a lead system constructed in accordance with one embodiment.

An implantable device 100, such as a lead 102 for use with an electrical stimulator 105, is illustrated in FIG. 1. The lead 102 includes a lead body 110, and at least one conductor 120 contained within the lead body 110. In one example, the at least one conductor 120 is an elongate conductor. The lead body 110 extends from a proximal end 112 to a distal end 114. The proximal end 112 of the lead is electrically coupled with the electrical stimulator 105, for example, with a lead connector 130 (FIG. 2).

In one option, the electrical stimulator 105 is a pulse sensor and generator that contains electronics to sense various electrical signals of the heart and also produce current pulses for delivery to the heart. The pulse sensor and generator may also contain electronics and software necessary to detect certain types of arrhythmias and to correct for them.

The lead 102 further includes, in one option, one or more electrodes 115. The one or more electrodes 115 are each electrically coupled with the at least one conductor 120. The electrode 115 allows for electrical signals to be delivered to the tissue from the electrical stimulator 105, or sensed from the tissue to the electrical stimulator 105. The lead 102 further includes, in one option, features to allow the lead body 110 to be fixated within a patient, for example, but not limited to, passive or active fixation features.

Figure 2:
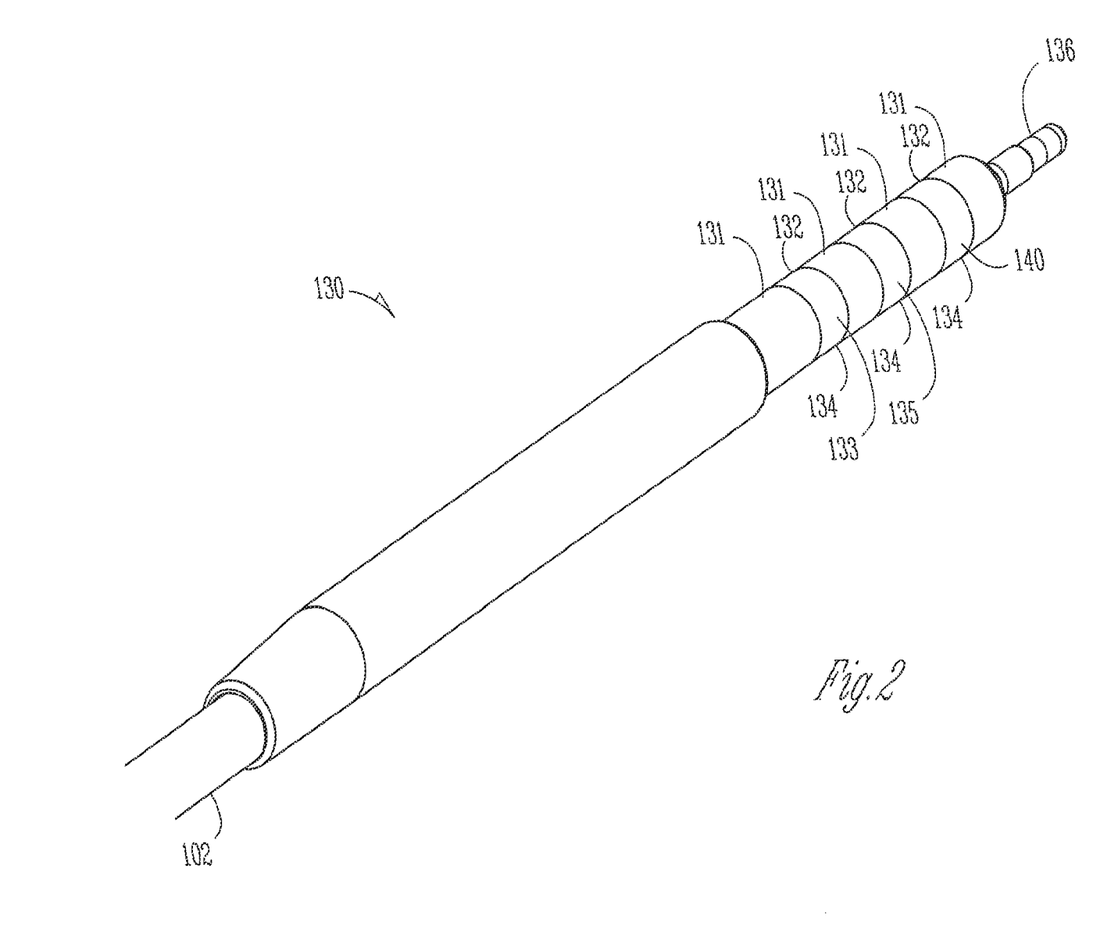
FIG. 2 is a perspective view of a portion of a lead constructed in accordance with at least one embodiment.

Referring to FIG. 2, a lead connector 130 is illustrated in greater detail, where one example of an in-line multipolar connector is illustrated. The lead connector 130 is configured to physically mate with a pulse sensor and generator (FIG. 1), and to electrically couple with the pulse sensor and generator. In one example, the lead connector 130 includes an electrode assembly 140 having one or more electrodes 132, such as, for example, three connector rings 134. The lead connector 130 further includes a connector pin 136. One or more of the electrodes 132 are interconnected with one another, in one example.

The lead connector 130 includes insulative material 131, and can have various visual properties. For example, the insulative material can be opaque, or substantially opaque, substantially clear, or clear. In one example, the lead connector 130 and the insulative material 131 allows for two or more electrodes 132 to be interconnected without being visible to the user, or at least visually discrete. For example electrodes 133 and 135 can be interconnected by an interconnect that is hidden by material such as the insulative material 131, as further discussed below. In another example, if the insulative material is clear, the interconnects may be geometrically small relative to the electrodes assisting in creating visual discreteness, where an interconnect may only be slightly visible upon close inspection of the lead connector 130.

FIGS. 3-11 illustrate several options for the electrode assembly 140. In one example, the electrode assembly 140 is an elongate structure that includes two or more electrodes, for example, at least a first electrode 150 and a second electrode 152, where the first electrode 150 and the second electrode 152 are defined in part by an outer surface, such as a diameter 154. The elongate structure extends from a first end 142 to a second end 144, where the elongate structure is defined in part by a longitudinal axis 146, and optionally a lumen 148 is disposed along the longitudinal axis 146. In one option, the first electrode 150 is disposed at the first end 142, and the second electrode 152 is disposed at the second end 144.

Figure 3:
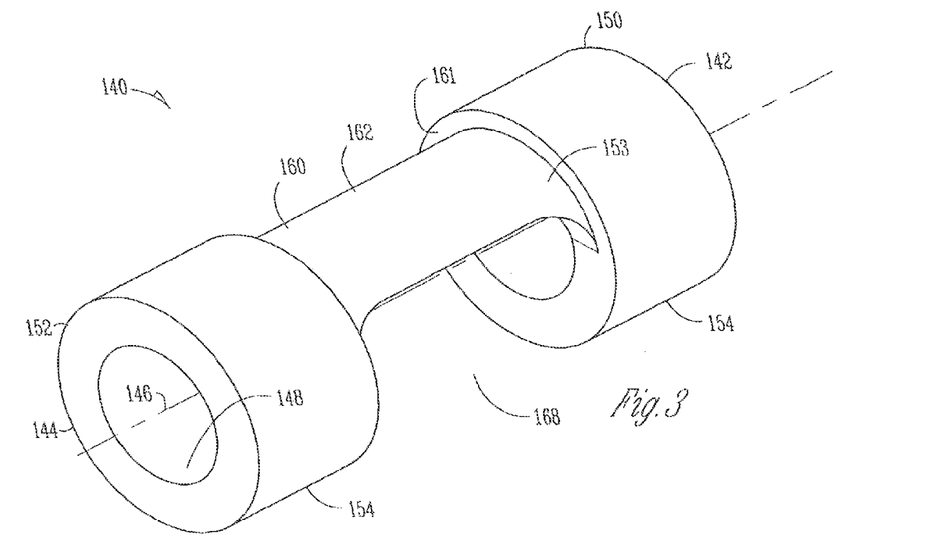
FIG. 3 is a perspective view of an electrode assembly constructed in accordance with at least one embodiment.
Figure 4:
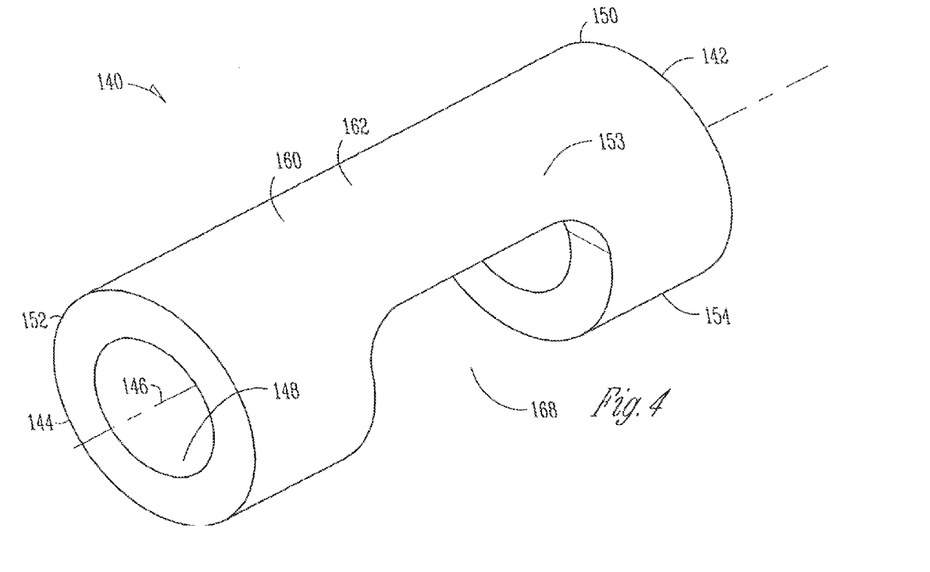
FIG. 4 is a perspective view of an electrode assembly constructed in accordance with at least one embodiment.
Figure 5:
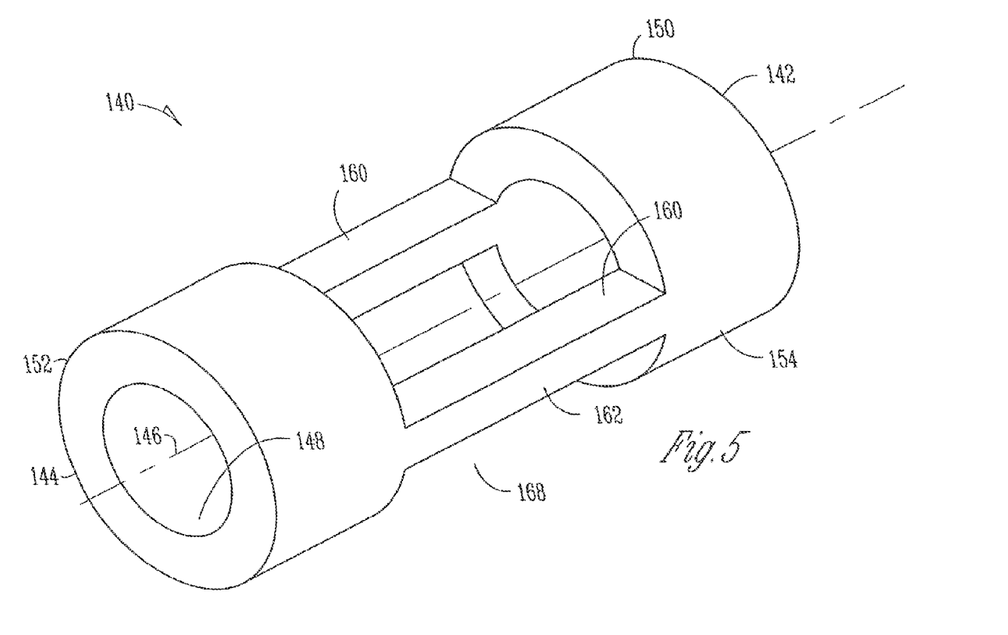
FIG. 5 is a perspective view of an electrode assembly constructed in accordance with at least one embodiment.
Figure 6:
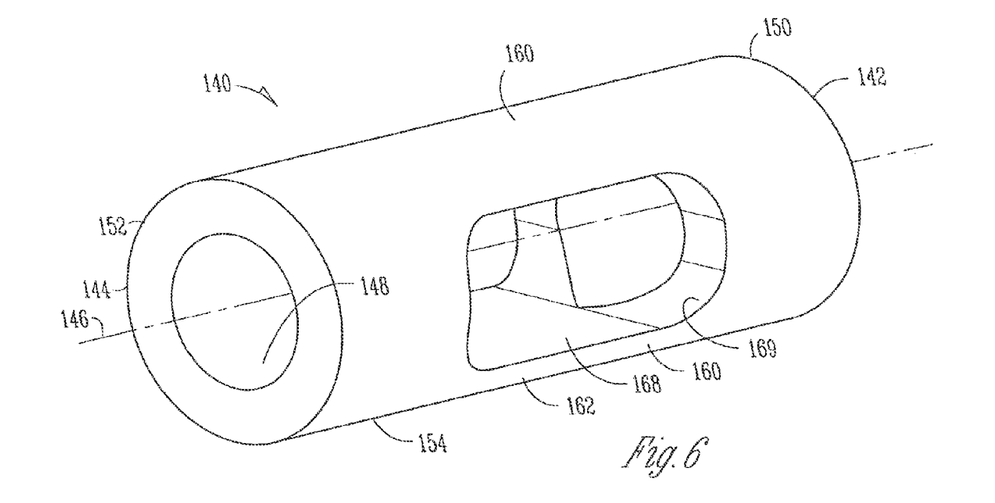
FIG. 6 is a perspective view of an electrode assembly constructed in accordance with at least one embodiment.

Disposed between the first electrode 150 and the second electrode 152 along an intermediate portion is at least one electrode interconnect 160, examples illustrated in FIGS. 3 and 4, where the at least one electrode interconnect 160 electrically and/or mechanically interconnects the first and second electrodes 150, 152. It should be noted that one or more interconnects can be disposed between the two or more electrodes. Furthermore, the interconnects can have various cross-sectional shapes, as further described below.

Referring to FIG. 3, in one option, the at least one electrode interconnect 160 is connected the first and second electrodes 150, 152 at a coupling 153, which optionally has a necked portion where the connection at the electrode is wider than the interconnect width. In another example embodiment, the intermediate portion includes a void and is recessed away from the outer diameter 154, for example as illustrated in FIG. 3. The recessed portion 161 has a variety of shapes. For example, the recessed portion 161 can be in the form of a void, an annular recess, or a cut out. The recessed portion 161 allows for the interconnect 160 that is between the electrodes to be hidden or disguised from view, for example, by placing material over the interconnect (FIG. 2).

In one example, the at least one electrode interconnect 160 substantially fixates the first electrode 150 and the second electrode 152 longitudinally and/or radially to one another. For example, the at least one electrode interconnect 160 prevents longitudinal and/or radial movement of the first electrode 150 relative to the second electrode 152. In one example, the at least one electrode interconnect 160 is formed of a substantially rigid material, assisting in maintaining the longitudinal and/or radial spacing of the first and second electrodes 150, 152. In another example, the at least one electrode interconnect 160 is made of substantially the same material as the first and/or second electrodes 150, 152. In yet another option, the at least one electrode interconnect 160 is made of a material that is more rigid than the first and/or second electrodes 150, 152. In yet another example, the elongate structure forming the first and second electrodes 150, 152 and the at least one electrode interconnect 160 are formed from a unitary piece of material, for example, but not limited to, molding or casting a single piece component, or removing material from a stock piece of material to form an interconnect between two or more electrodes, or forming a void along an elongate piece of material.

The at least one electrode interconnect 160 is defined in part by an interconnect diameter 162. In one or more options, for example as shown in FIGS. 3, 7, 8, 9, 10, and 11, the interconnect outer surface or diameter 162 is less than the electrode diameter 154. This can allow for insulative material to be disposed thereover providing a visually discrete unit, and also can allow for providing an isodiametric component. In other options, as shown for example in FIGS. 4-6, the interconnect diameter 162 is substantially the same as the electrode diameter 154.

The electrode interconnect 160 is disposed along an intermediate portion of the elongate structure, and has a variety of cross-sectional shapes. For example, FIGS. 3, 4, 6, and 11 illustrate example interconnects having an arcuate shape, for example similar in shape to the electrode. In a further option, the interconnect has a circular cross-section, as shown in FIG. 11. Other options for interconnects include, but are not limited to, those illustrated in FIGS. 5, and 7-10, where the interconnect includes one or more planar sides. Further options include having multiple interconnects disposed between the electrodes, for example as illustrated in FIGS. 5, 7-10.

Various methods can be used to form the electrode assembly 160. For example, a method for forming one or more of the electrode assemblies discussed above, includes providing an elongate structure of electrically conductive material, where the elongate structure extends from a first end to a second end and defined in part by an outer perimeter, and removing a portion of material from the elongate structure, for example to form a void between two or more electrodes. Examples of such elongate structure include stock material, for example, that is extruded with a preformed lumen therein, or electrically conductive material. The material is removed from the elongate structure, for example, by EDM, machining, broaching, grinding, or other material removal processes to form a void such as a cut out, a slot, a slotted portion, or a recessed portion, as discussed above and below. In one option, material is removed from more than one location along the outer perimeter of the intermediate portion to form, for example, multiple interconnects between the first and second electrodes. For example, multiple locations can have material removed to form two, three, or more interconnects between the electrodes. In removing the material, additional material can be removed from an outer diameter surrounding the interconnect such that the interconnect has an outer diameter that is smaller than the outer diameter of the electrodes.

The interconnect can be formed in a variety of different manners, resulting in a variety of structures and shapes for the interconnect. In one option, the interconnect 160 is formed by the removal of material from the outer perimeter of the elongate structure, and in one example forms a void such as a cut out 168 (FIG. 3). The cut out 168, in one option, can be in the form of a slot or a slotted portion 169 (FIG. 6) between the first and second electrodes 150, 152, and/or allowing for a substantially constant outer diameter for the interconnect and the first and second electrodes 150, 152. In another example, two or more interconnects are formed by milling a slot 169 within the elongate structure, where the slot 169 extends substantially traverse, in one option, relative to axis 146. The slot 169 can extend entirely through the elongate structure, or can extend only partially through the elongate structure.

Figure 7:
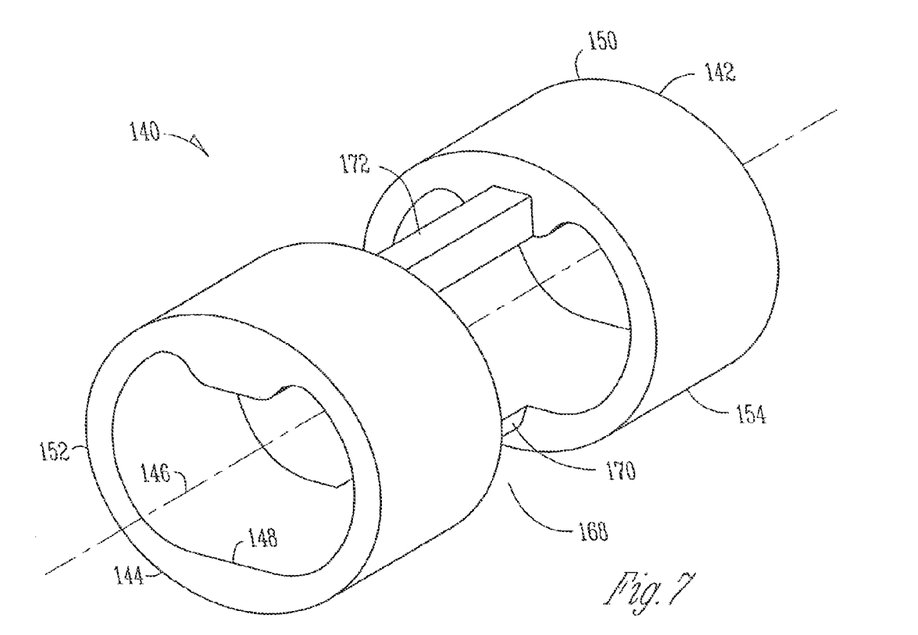
FIG. 7 is a perspective view of an electrode assembly constructed in accordance with at least one embodiment.

In one option, the at least two interconnects 170, 172 are connected with the first and second electrodes in the same way, for example by forming a unitary device or of a unitary piece of material, as illustrated in FIG. 7. In another option, the at least two interconnects 170, 172 have a different cross-section from one another, and/or are connected with the first and second electrodes 150, 152 in different manners, as illustrated in FIG. 7. For example, a first interconnect 170 is formed by removing material from an elongate piece of material, and a second interconnect 172 is formed by coupling a separate non-integral component between the first and second electrodes 150, 152.

Other interconnects can be used to create interconnected electrodes, such as rings, where the interconnects are separate components such as a rigid rod, a rigid tube, a wire, such as a somewhat flexible or rigid wire, or a flexible cable. These interconnects can have different material than the electrodes. These separate interconnect components can be joined with the electrodes through a material joining process including welding, staking, crimping, brazing, soldering, etc.

Figure 8:
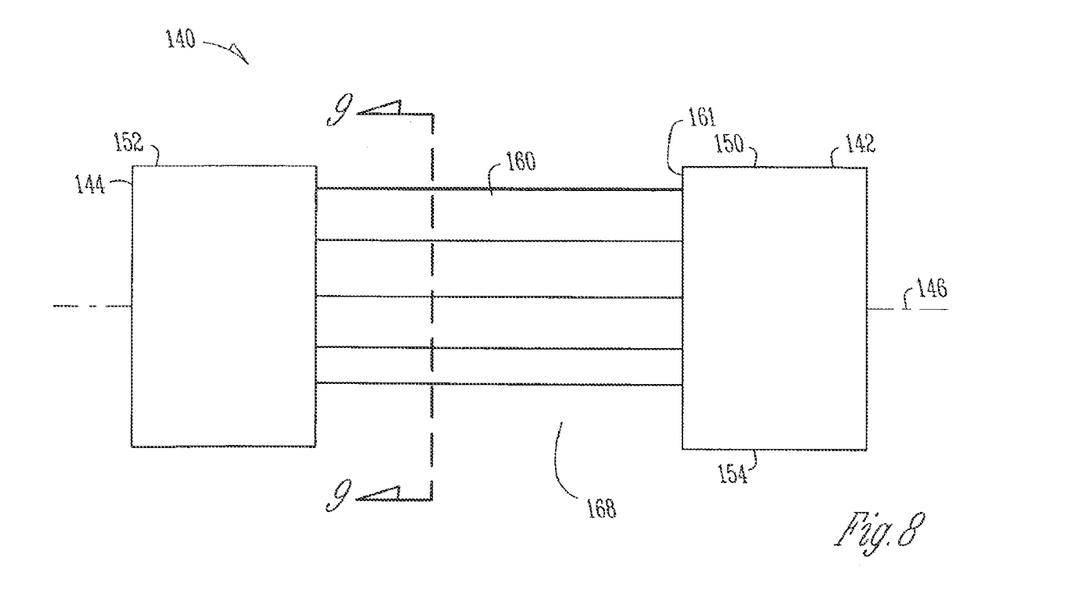
FIG. 8 is an elevational view of an electrode assembly constructed in accordance with at least one embodiment.
Figure 9:
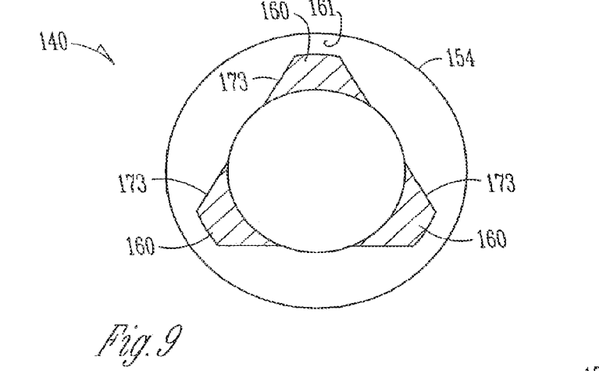
FIG. 9 is a cross-sectional view of an electrode assembly taken along 9-9 of FIG. 8 constructed in accordance with at least one embodiment.
Figure 10:
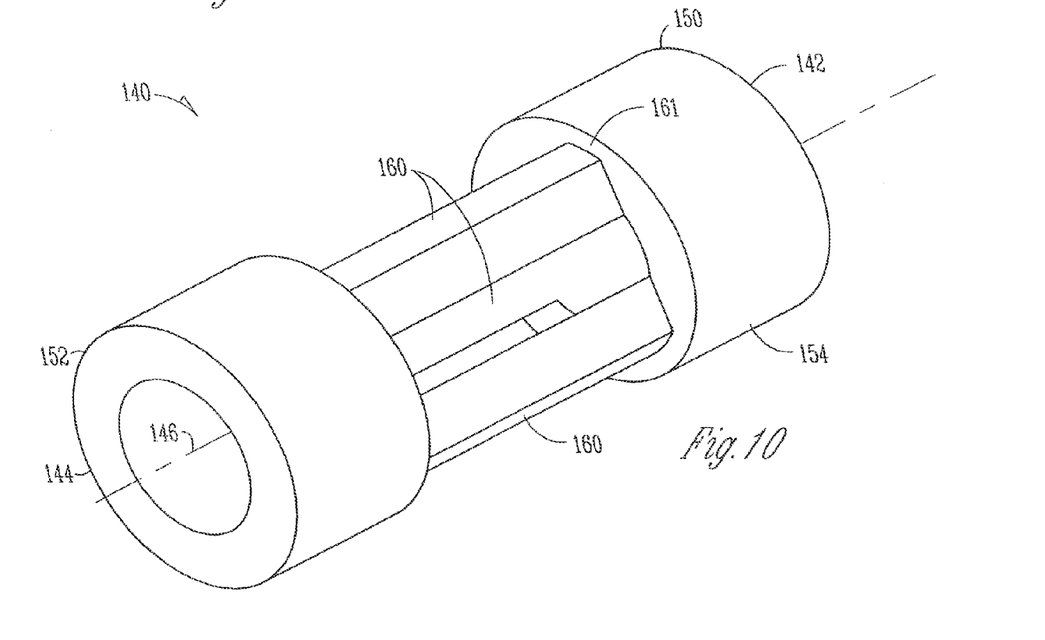
FIG. 10 is a perspective view of an electrode assembly constructed in accordance with at least one embodiment.
Figure 11:
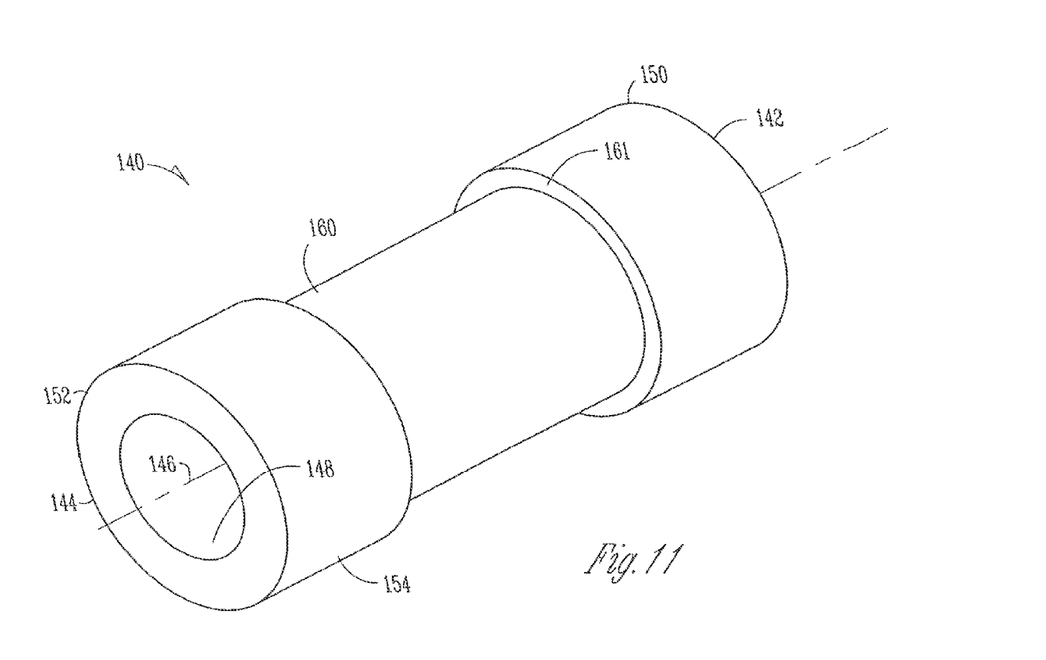
FIG. 11 is a perspective view of an electrode assembly constructed in accordance with at least one embodiment.

FIGS. 8-10 illustrate additional examples of electrode assemblies formed using various methods including material removal processes. Although it should be noted that the electrode assemblies of FIGS. 8-10 can be formed using other processes, including, but not limited to, molding or casting. One example for forming the at least three interconnects 160 includes removing a plane of material within the elongate structure at three different locations, resulting in angled planes 173 on a side of the interconnects 160. FIG. 11 illustrates yet another option for the interconnect 160. Another example for forming the interconnect includes turning down an outer surface along an intermediate portion of an elongate structure to form the interconnect 160 as shown in FIG. 11.

The electrode assemblies can be formed in other manners, for example using molding or casting techniques, with or without secondary material removal processes such as machining. These techniques will allow for interconnected electrodes, such as electrode rings, to be formed into a component of one, unitary piece of material, having any of the structure as described above, and as illustrated in FIGS. 3-11. For example, the elongate structure of the electrode assembly can be molded or cast with a void to form a cut out or recess or recessed portion therein. Other options include forming at least one lumen substantially parallel with a longitudinal axis of the electrode assembly. These forming techniques would further allow for an electrode assembly that can maintain its longitudinal and/or radial spacing of electrodes.

During use of the device, the lead having the lead connector and electrode assembly, including the various options discussed above, is introduced within the vasculature of a patient. The energy source, such as the pulse generator and sensor, is implanted subcutaneously within the patient. The lead connector and electrode assembly are electrically coupled with the energy source. For example, the lead connector is inserted into a socket of the energy source, and the electrode assembly, including the electrodes 150, 152 form an electrical connection within the energy source.

Advantageously, the lead connector including the various electrode assemblies discussed above, can improve reliability in electrode performance, for example, of in-line multipolar lead connectors. The electrode assembly of the lead connector can be made faster, more cost-effectively, and using less complex processes. Furthermore, the manufacturability and dimensional control, for example longitudinal and radial dimensions, are improved with the above-discussed examples. Additionally, the interconnect is visually discrete or substantially invisible to the user.

It is to be understood that the above description is intended to be illustrative, and not restrictive. Although the use of the implantable device has been described for use with a lead in, for example, a cardiac stimulation system, the implantable device could as well be applied to other types of body stimulating systems. It should be noted that the above discusses electrode assemblies having two or more electrodes, and one or more interconnects, and is not limited to a particular number of electrodes and/or interconnects. Many other embodiments will be apparent to those of skill in the art upon reviewing the above description. The scope should, therefore, be determined with reference to the appended claims, along with the full scope of equivalents to which such claims are entitled.

What is claimed is:

1. An apparatus for coupling an implantable lead to an implantable stimulator, the apparatus comprising:
    a lead connector located at a proximal end of the implantable lead, the lead connector having an electrode assembly including an elongate unitary member extending from a first end to a second end, and an intermediate portion located between the first and second ends;
    the first end forming a first electrode and the second end forming a second electrode; and
    the intermediate portion including a plurality of elongate electrode interconnects extending between the first and second electrodes, and at least one void disposed between the first and second electrodes.

2. The apparatus of claim 1, wherein an outer perimeter of at least one electrode interconnect is substantially flush with an outer circumference of the first and second electrodes.

3. The apparatus of claim 1, wherein an outer perimeter of at least one electrode interconnect is recessed away from an outer circumference of the first and second electrodes.

4. The apparatus of claim 1, wherein at least one of the electrode interconnects electrically connects the first electrode to the second electrode.

5. The apparatus of claim 1, wherein the electrode interconnects extend lengthwise along a longitudinal axis of the elongate unitary member.

6. The apparatus of claim 1, wherein the electrode interconnects are configured to prevent longitudinal and radial movement of the first electrode relative to the second electrode.

7. The apparatus of claim 1, wherein the electrode interconnects, the first electrode, and the second electrode are formed of a single, unitary member.

8. The apparatus of claim 1, wherein each electrode interconnect includes one or more planar sides.

9. The apparatus of claim 1, wherein the first and second electrodes each comprise a first material, and wherein the electrode interconnects each comprise a second material having a rigidity greater than the first material.

10. The apparatus of claim 1, wherein the void includes a recessed portion disposed along an outer perimeter of the intermediate portion.

11. The apparatus of claim 1, wherein the first and second electrodes are annular-shaped electrodes.

12. An apparatus for coupling an implantable lead to an implantable stimulator, the apparatus comprising:
- a lead connector located at a proximal end of the implantable lead, the lead connector having an electrode assembly including an elongate unitary member extending from a first end to a second end, and an intermediate portion located between the first and second ends;
- the first end forming a first electrode and the second end forming a second electrode; and
- the intermediate portion including a first elongate electrode interconnect extending lengthwise along a longitudinal axis of the elongate unitary member between the first and second electrodes, and a second elongate electrode interconnect extending lengthwise along the longitudinal axis between the first and second electrodes, and at least one void disposed between the first and second electrodes;
- wherein the first and second elongate electrode interconnects are configured to prevent longitudinal and radial movement of the first electrode relative to the second electrode.

13. An electrode assembly for an implantable lead, the electrode assembly comprising:
- an elongate unitary member extending from a first end to a second end, and including an intermediate portion located between the first and second ends;
- the first end forming a first electrode and the second end forming a second electrode; and
- the intermediate portion including a plurality of elongate electrode interconnects extending lengthwise along a longitudinal axis of the elongate unitary member between the first and second electrodes, and at least one void disposed between the first and second electrodes.

14. The assembly of claim 13, wherein an outer perimeter of at least one electrode interconnect is substantially flush with an outer circumference of the first and second electrodes.

15. The assembly of claim 13, wherein an outer perimeter of at least one electrode interconnect is recessed away from an outer circumference of the first and second electrodes.

16. The assembly of claim 13, wherein at least one of the electrode interconnects electrically connects the first electrode to the second electrode.

17. The assembly of claim 13, wherein the electrode interconnects are configured to prevent longitudinal and radial movement of the first electrode relative to the second electrode.

18. The assembly of claim 13, wherein each electrode interconnect includes one or more planar sides.

19. The assembly of claim 13, wherein the first and second electrodes each comprise a first material, and wherein the electrode interconnects each comprise a second material having a rigidity greater than the first material.

20. The assembly of claim 13, wherein the first and second electrodes are annular-shaped electrodes.

* * * * *